United States Patent [19]
Hamm et al.

[11] Patent Number: 5,382,914
[45] Date of Patent: Jan. 17, 1995

[54] PROTON-BEAM THERAPY LINAC

[75] Inventors: Robert W. Hamm, Pleasanton, Calif.; Kenneth R. Crandall, Corrales; James M. Potter, Los Alamos, both of N. Mex.

[73] Assignee: AccSys Technology, Inc., Pleasanton, Calif.

[21] Appl. No.: 879,966

[22] Filed: May 5, 1992

[51] Int. Cl.$^6$ .............................................. H01J 25/10
[52] U.S. Cl. ...................................................... 315/505
[58] Field of Search ................................. 328/227, 233

[56] References Cited
U.S. PATENT DOCUMENTS 5,014,014  5/1991  Swenson ............................ 328/233
5,113,141  5/1992  Swenson ............................ 328/233

Primary Examiner—Sandra L. O'Shea
Attorney, Agent, or Firm—Kolisch Hartwell Dickinson McCormack & Heuser

[57] ABSTRACT

A compact proton-beam therapy linac utilizing a linear, cascaded organization including a proton source, a radio-frequency-quadrupole (RFQ) linac coupled to the output of the source, a stepped-frequency (around 500- to around 1000-MHz), low-peak-beam-current (around 100- to around 300-$\mu$A) drift-tube linac (DTL) coupled to receive the output of the RFQ, and a plural-stage, low-peak-beam-current stage-switchable, side-coupled linac (SCL) coupled to the output of the DTL for producing the ultimate output proton-therapy beam.

13 Claims, 2 Drawing Sheets

PROTON-BEAM THERAPY LINAC

BACKGROUND AND SUMMARY OF THE INVENTION

This invention relates to a proton-beam therapy linac, and more particularly to such a unit which is capable of offering high-level performance in an extremely compact and relatively low-cost form.

With respect to the disclosure and discussion which follow herein, several prior art documents are useful, and are referred to in the text. These references are herebelow listed in the order in which they are mentioned: (1) J. M. Sisteron. "Clinical Use of Protons and Ion Beams from a World-Wide Perspective," NIM B40/41, pp. 1350–1353, 1989; (2) J. M. Slater, "Developing a Clinical Proton Accelerator Facility; Consortium-Assisted Technology Transfer," Proceedings of this conference: (3) P. Mandrillon, "High Energy Medical Accelerators," EPAC-90 Proceedings, Nice, France, June 1990, pp. S4–S8; (4) G. Lawrence (Los Alamos National Lab), Oral Presentation, PTCOG-13, Berkeley, Calif., November 1990; and (5) M. Goitein, "Proton Beam Intensity," Report of the Facilities Working Group, PTCOG, September 1987.

Exploring the background of this invention, the use of electron linacs to great cancer has experienced an explosive growth during the past two decades or so, with more than six thousand accelerators (linacs) estimated now to be in use around the world. Although it is widely recognized that proton beams have major advantages over these photon and electron-beam machines, extensive use of proton beams has not been realized due to the lack of dedicated facilities. However, more than nine thousand patients have by today been treated worldwide with ion beams at institutions with physics research accelerators (see Reference Document 1). The success of these programs has led to significant interest within the medical community in dedicated proton treatment facilities. The first such system, a 250-MeV synchrotron at Loma Linda Medical Center in California, is now treating patients (see Reference Document 2). A full description of the construction and operation of this system is found in U.S. Pat. No. 4,870,287, issued to Cole et al. on Sep. 26, 1989 for MULTI-STATION PROTON BEAM THERAPY SYSTEM.

As is pointed out by Mandrillon (Reference Document 3), the key requirements for a proper, dedicated proton therapy accelerator are: (1) that is must be compact enough for installation in a large hospital; (2) that it must be highly reliable and easy to operate; (3) that it must be compatible with beam scanning and isocentric gantries; and (4) that it must have a maximum energy capability greater than 200-MeV, Mth an intensity sufficient to treat large tumors in short irradiation times. Other important considerations include safety, ease of maintenance, and costs (equipment, facility and operation).

While the synchrotron facility at Loma Linda appears to be technically viable, its cost and complexity have caused radiation therapy groups to consider alternative approaches.

Conventional protons linacs are routinely used for injecting beams into synchrotrons, but they are considered to be too expensive and too powerful for low-current, high-energy proton acceleration. However, a "proton version" of the conventional S-band (operating at frequencies around 3000-MHz) electron linacs used for radiation therapy, employed according to the preferred embodiment of the invention disclosed and described herein, satisfies all of the requirements for an appropriate, dedicated proton therapy accelerator. While cascaded linacs have previously been employed for accelerating protons, high-frequency structures (i.e. those operating at around 3000-MHz) have been considered only for accelerating electrons. It is possible, for example, to use side-coupled linac structure with an operating frequency near 3000-MHz (S-band), for this application due to the very low current required from the same. The use of multiple, side-coupled linac (SCL) tanks, and rf power amplifiers, allows for variable output energy. A compact, high-frequency drift-tube linac (DTL) having a stepped-frequency (dual, 1:2 frequency ratio herein) can be used, and is used in the present invention, as the injector to the SCL at 70-MeV, with a conventional radio-frequency-quadrupole (RFQ) linac functioning as the DTL's input. It is the cascaded organization and arrangement of such an SCL, stepped-frequency DTL and RFQ for the acceleration of low-peak-current proton beams (see Table 1 below) that forms the foundation of the system of the present invention.

Various other important features, objects and advantages which are offered by the linac of the present invention will become more fully apparent as the description That now follows is read in conjunction with the accompanying drawings.

DETAILED DESCRIPTION OF, AND BEST MODE FOR IMPLEMENTING, THE INVENTION

Figure 1:
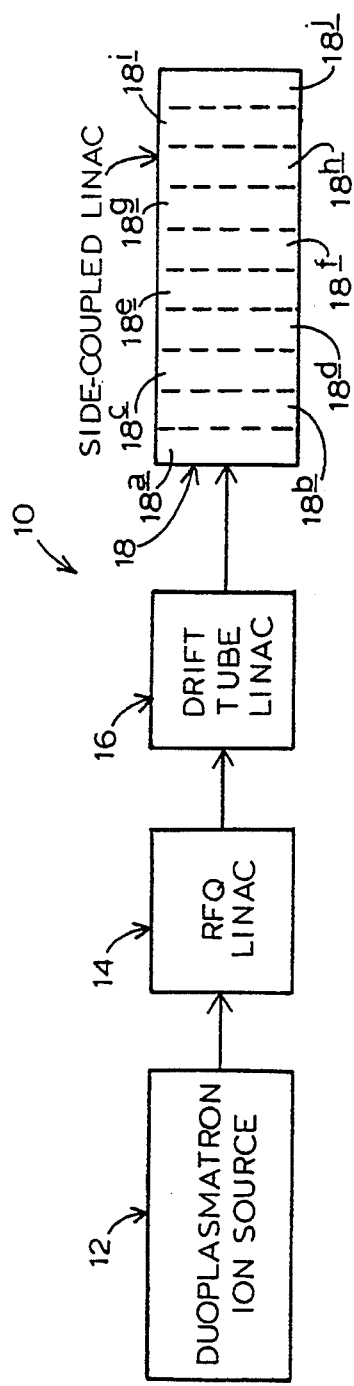
FIG. 1 is a simplified block/schematic diagram illustrating the cascaded, cooperative organization of components that makes up the proton therapy linac proposed by the present invention.
Figure 2:
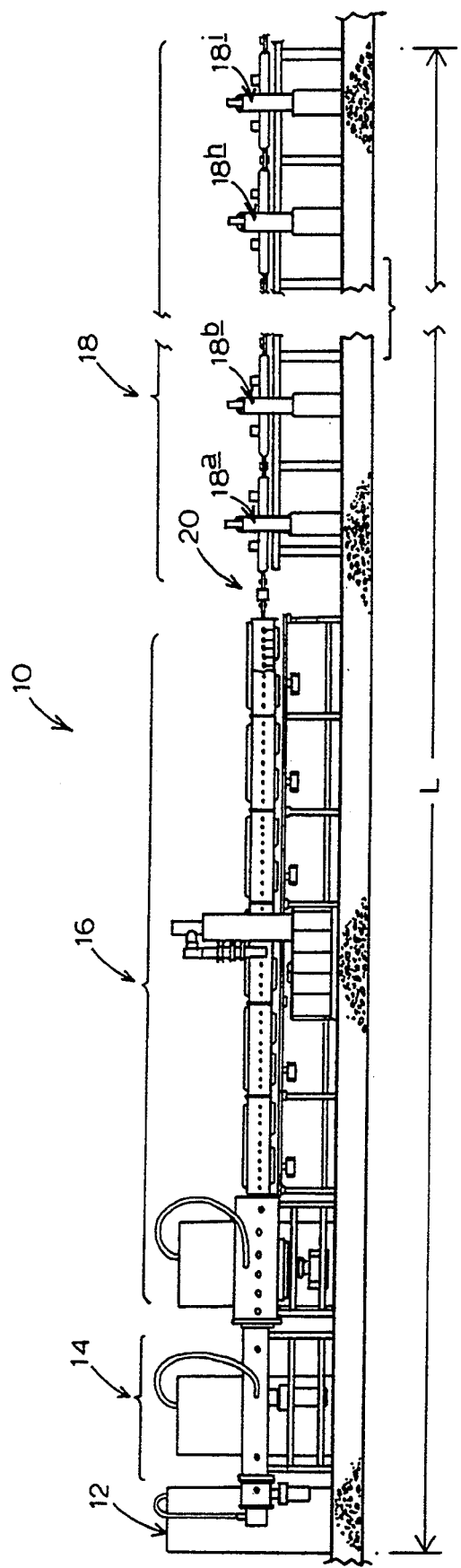
FIG. 2 is a fragmentary, schematic side elevation further illustrating the organization depicted in FIG. 1.

Turning attention now to FIGS. 1 and 2, indicated generally at 10 is a proton-beam therapy linac (PTL) constructed in accordance with the present invention. PTL 10 is an elongate, linear, and quite compact structure which is formed by the cascaded interconnection of four basic sub-units, including a duo-plasmatron ion (proton) source 12, a radio-frequency-quadrupole linear accelerator (RFQ) 14, a drift-tube linear accelerator, or linac, (DTL) 16, and a side-coupled linear accelerator, or linac, (SCL) 18. Each of these four sub-units is, individually, conventional in construction and well understood by those skilled in the art. Accordingly, in the descriptive material below, we assume a certain basic working knowledge of the constructions and operations of these devices. The assemblage, however, to make up high-frequency, low-peak-beam-current PTL 10 as a whole is entirely new. For example, it is totally new in the art, and has been questioned even as possible in the immediate past, to use S-band electron linac structure for the acceleration of a beam of protons. Use, as proposed herein, of a stepped-frequency DTL intermediate the RFQ and the SCL significantly has opened the door to the employment of such S-band structure. And, with the S-band SCL as the final accelerator stage, continuous energy-level control, and safe current-level delivery, to a patient are possible. This assemblage herein has an overall, compact length, indicated at L in FIG. 2, of only about 28-meters. Overall specifications for DTL 10 are set forth in Table 1:

TABLE 1

Preliminary Specifications for a Dedicated Proton Therapy Linac

| | | |
|---|---|---|
| Accelerated particle | H+ | |
| Maximum beam energy | 250 | MeV |
| Minimum beam energy | 70 | MeV |
| No. energy increments | 11 | |
| Peak beam current | 100–300 | μA |
| Beam pulse width | 1–3 | μsec |
| Repetition rate | 100–300 | Hz |
| Average intensity | 10–270 | nA |
| Beam emittance (norm.) | <0.1 | πmm-mrad |
| Beam energy spread | ±0.4 | % |
| Max. rf duty factor | 0.125 | % |
| Peak rf power | 62 | MW |
| Maximum input power | 350 | kW |
| Stand-by power | 25 | kW |
| Accelerator length | 28 | meters |

Beginning at the left side of linac 10 in FIGS. 1 and 2, proton source 12 has associated with it a conventional electrostatic einzel lens (not specifically shown), and functions to inject up to 1-ma of 30-KeV protons into RFQ 14, which has a length of about 2.43-meters. RFQ 14 is a 3-MeV device, operating at a frequency of 499.5-MHz, with a vane-to-vane voltage of 50-kV, a calculated beam transmission of 96%, and a required peak rf power of 0.2-MW. RFQ 14 operates as a "chopper" for creating a pulsed proton beam from the unpulsed beam furnished by source 12.

Drift tube linac (DTL) 16 has two discreet tanks which are referred to in this application as a "first tank" and a "main tank". The RFQ 14 linac is closely coupled to the first tank of DTL 16, both of which operate at 499.5-MHz. The first four quadrupole magnets in this tank are used for matching the beam transversely from the RFQ into the DTL. This first tank has an output energy of 12.5-MeV, is only 1.187-meters long (with twenty-six cells), and requires a peak rf power of 1.0-MW. There is no longitudinal matching into this DTL tank and as a consequence, the beam rotates in longitudinal phase space.

The synchronous phase of the structure is ramped instead to produce a good longitudinal match into the main DTL tank which is operated, according to an important feature of the invention, at a stepped-up substantially 1:2 frequency ratio (relative to the first tank) frequency around 1,000-MHz. It is the presence in the structure now being described of the stepped-up-frequency main DTL tank which allows use, in the final stage, of SCL 18 operating at around 3000-MHz; In the specific illustration now being given, the operating frequency is precisely 999-MHz. The last four quadrupole magnets are used to match the beam transversely into the main DTL tank, which therein accelerates the proton beam from 12.5-MeV to 70.4-MeV over a length of 7.92-meters. This DTL tank has a total of ninety-eight accelerating cells, and requires a peak rf power of 8.2-MW. The synchronous phase is constant at −30°, and there is a permanent-magnet-quadrupole assembly in every other drift tube, with the magnetic field gradient tapered down the length of the DTL. The bore in the drift tubes in both sections of the DTL is only 1-centimeter in diameter, but the beam transmission is calculated to be 100%, even if the quadrupole magnets have random displacements as large as about ±0.005-inches.

The largest section of linac 10 is SCL 18 which operates at 2997-MHz. Between DTL 16 and SCL 18, and indicated generally at 20 in FIG. 2, is a 1-meter matching section of two quadrupole magnets and a single SCL tank, operating at a synchronous phase of −90°. This short tank is 0.2-meters long, and requires 0.3-MW of rf power.

SCL 18 consists herein of up to ten accelerator modules, indicated at 18a, 18b, 18c, 18d, 18e, 18f, 18g, 18h, 18i, 18j. Each module takes the form of four accelerating tanks brazed together using eleven, equal-length accelerating cells with a beam bore of 4-millimeters diameter, and with each module powered by a 7-MW S-band klystron system. The four accelerating sections are connected with 3βλ/2 bridge couplers to allow a single permanent magnet quadrupole to be placed between them. The quadrupole focusing gradient is ramped in steps along the lengths of the modules. The total length of SCL 18 is 14-meters.

Figure 3:
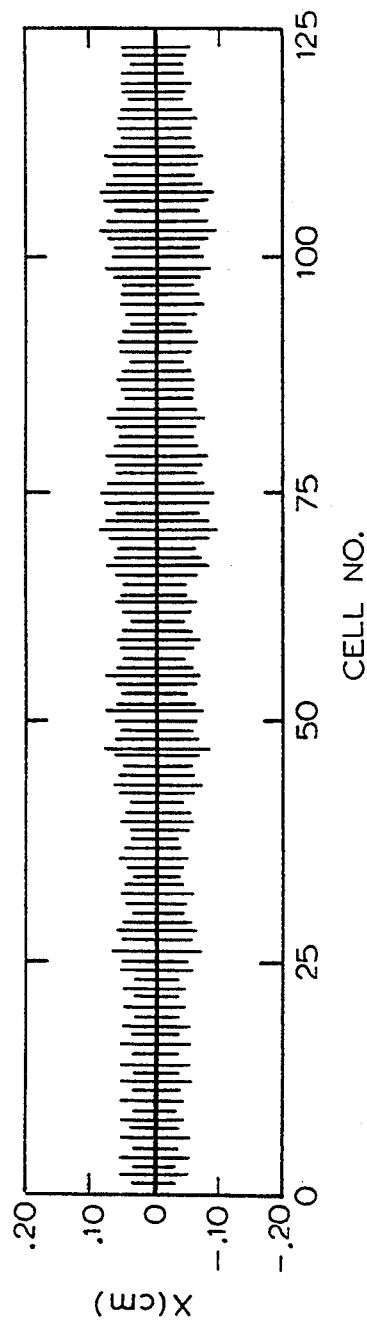
FIG. 3 illustrates, on a cell-by-cell basis, the calculated beam profile through a DTL employed in the proposed system.
Figure 4:
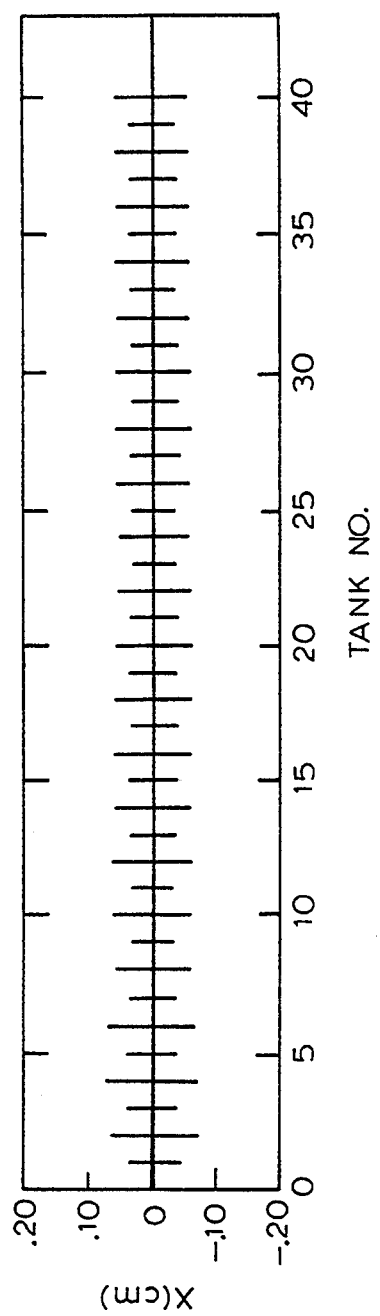
FIG. 4 illustrates, on a tank-by-tank basis, the calculated beam profile through an SCL employed in the proposed system.

Turning attention for a moment to FIGS. 3 and 4 in the drawings, the calculated 250-MeV beam profile through DTL 16 and SCL 18 are shown, respectively. No beam is lost during acceleration. Calculations also show that the 70-MeV beam from the DTL can be transmitted through the SCL without any losses, or it could be deflected in the transition region to a separate treatment area.

Each section of linac 10 is powered by a separate rf power amplifier driven by a master oscillator and timing circuit. The RFQ and the first DTL tank are powered by commercially available, rugged, planar triode amplifiers. The main DTL tank is powered by a single 10-MW klystron. This klystron is a conventionally, commercially available L-band unit modified appropriately to operate at 999-MHz.

The largest number of rf power systems employed in linac 10 is required for SCL 18. Ten S-band klystron systems are used, and these are readily available commercial production models manufactured and made available for medical electron linacs. The power supply and pulser system for the klystrons is capable of pulse widths of up to 5-μsec, and can be operated at a duty factor of 0.0012. Experience has shown that each klystron typically requires 25-kW of input ac power when operating at its maximum duty factor. Each klystron is a self-contained unit that is appropriately interfaced to the master driver chassis.

Looking for a moment at vacuum considerations, source 12 and RFQ 14 are pumped by commercially available cryopump systems for effective handling of the hydrogen gas load from the source (<0.5 sccm). DTL 16 is pumped by clean, low-maintenance ion pumps, since the gas load in this section, which will seldom be opened to atmospheric pressure, is minimal. The SCL modules are also pumped by ion pumps, just as in conventional electron linacs, but with slightly larger-capacity pumps because of the fact that these modules are not sealed. The rf power windows are mounted in the middle-bridge coupler of each SCL module so that they are readily field-replaceable. Suitable vacuum valves are provided for localizing sections in linac 10 for necessary repair or service. The presence of such "localizing" valves speeds up pump-down and rf conditioning times.

Linac 10 is operated, in a sense, as a large version of a conventional modern medical electron linac. The level of control necessary to achieve this type of operation is minimal, since all of the timing and rf power stabilization is hard-wired into the system. For example, it is easily operated by a wide variety of readily available, modern, PC-based computer systems.

In a practical setting, after initial start-up each day, control of linac 10 could, for example, be transferred to the using facility's treatment control system for delivery of the output beam to various treatment areas, and for switching on and off of the rf system to control patient dosage. Such a stand-by (switching on and off) mode would greatly reduce the required input power to the system, while not affecting in any way the reliability or instantaneous availability of the proton beam.

Beam delivery to selected treatment areas can be achieved with modest transport elements, since the diameter of the output beam from the system is less than 2-millimeters, and since the emittance in both planes is less than $0.1$-$\pi$cm-mrad. Since a magnet gap of 1.0-centimeters or less would be required for the beam, a conventional isocentric gantry can also be constructed using very small magnets, i.e. less than 1-ft$^3$ (see Reference Document 4). Beam profiles (calculated) through DTL 16 and SCL 18 are as indicated in FIGS. 3 and 4, respectively.

The proton-beam therapy linac thus proposed by the present invention provides an economical, reliable, compact, easy-to-use accelerator for dedicated cancer-therapy facilities. By using the RFQ linac as a "chopper" for pulsing the proton beam delivered by source 12, the current-per-pulse in linac 10 can be controlled using the beam pulse width. By varying the beam which is injected into the RFQ using the electrostatic lens mentioned above, and by varying the beam pulse width and pulse repetition rate, the average output beam intensity can be varied from a few nA up to a few hundred hA. Goitein (see Reference Document 5) has indicated that these currents are adequate for treating a wide range of tumors. Similarly, by turning on one or more of the SCL klystrons, the output beam energy can be varied in eleven easily controlled steps, from 70-MeV to 250-MeV, with each step being approximately 18-MeV. Continuous beam energies can be achieved between these steps with little loss in intensity by the use of well-known degrading foils.

One of the keys to the reliability, economy and clinical capability of the linac therapy system proposed by the present invention is that the unique cascading assemblage of the system allows the use of components based upon well-established and available SCL cavities and rf power systems, making practically possible the use of such SCL S-band structure for proton beam acceleration is the employment, in the "cascade" of the stepped-frequency DTL described herein. The use of such proven components makes the proposed linac-10 configuration similar to that of existing high-energy medical electron linacs. The maximum duty factor of linac 10 is dictated by the SCL rf power systems, and is more than adequate for the maximum current required. For example, as is shown in Table 1, even though the peak rf power requirement is large, the maximum input ac power requirement is much lower than that required for other types of accelerators operating at the same energy level. Much of the input power is required for the rf systems, and, since they are turned off between treatments, stand-by power needed for system 10 is very low. Certainly prominent among the unique features contributing to low cost and compactness in system 10 is the use therein of high-frequency (i.e., about 1000-MHz) DTL 16.

While a preferred embodiment of the invention has been described hereinabove, we appreciate that certain variations and modifications may be made without departing from the spirit of the invention. For example, other combinations of conventional RFQ and DTL frequencies will allow the use of other commercial S-band cavities and RF power systems operating at frequencies such as 357 MHz, 714 MHz and 2856 MHz.

It is claimed and desired to secure by Letters Patent:

1. A compact proton-beam medical therapy linac (PTL) comprising
   a proton source,
   a radio-frequency quadrupole linear accelerator (RFQ) operatively coupled to said source for forming an accelerated beam of protons furnished by the source,
   a stepped-frequency drift-tube linear accelerator (DTL) having a lower-frequency first tank structure operatively coupled to the output of said RFQ for receiving an injection from the latter of a proton beam formed and accelerated by the same, and a higher-frequency main tank structure coupled to said first tank structure, and
   a side-coupled, S-band linear accelerator (SCL) operatively coupled to the main tank structure of said DTL for receiving an injection from the latter of a proton beam accelerated by the same, and for producing an output proton therapy beam,
   interposition of said stepped-frequency DTL between said RFQ and SCL enabling viable employment of said SCL for accelerating such a proton beam.

2. The PTL of claim 1, wherein said main accelerating tank structure is constructed to operate at a frequency of about 1000-MHz.

3. The PTL of claims 1 or 2, wherein said SCL includes plural, cascaded, independently selectively operable accelerator modules.

4. The PTL of claim 3, wherein said modules operate at a frequency of about 3000-MHz.

5. The PTL of claims 1 or 2 which is structured to operate at a peak beam current of around 100- to around 300-$\mu$A.

6. The PTL of claim 3 which is structured to operate at a peak beam current of around 100- to around 300-$\mu$A.

7. The PTL of claim 4 which is structured to operate at a peak beam current of around 100- to around 300-$\mu$A.

8. The PTL of claims 1 or 2 which has an elongate, linear configuration, with an overall length no greater than about 28-meters.

9. The PTL of claim 3 which has an elongate, linear configuration, with an overall length no greater than about 28-meters.

10. The PTL of claim 4 which has an elongate, linear configuration, with an overall length no greater than about 28-meters.

11. The PTL of claim 5 which has an elongate, linear configuration, with an overall length no greater than about 28-meters.

12. The PTL of claim 6 which has an elongate, linear configuration, with an overall length no greater than about 28-meters.

13. The PTL of claim 7 which has an elongate, linear configuration, with an overall length no greater than about 28-meters.

* * * * *